United States Patent [19]

Kawabe et al.

[11] Patent Number: 5,153,183
[45] Date of Patent: Oct. 6, 1992

[54] METHYLENEDIPHOSPHONIC ACID COMPOUNDS AND METHODS OF USE FOR THE TREATMENT OF RHEUMATISM AND OSTEOPHOROSIS

[75] Inventors: Norio Kawabe, Otsu; Keijiro Takanishi; Shu Matsumoto, both of Kamakura, all of Japan

[73] Assignee: Toray Industries, Inc., Japan

[21] Appl. No.: 663,958

[22] PCT Filed: Aug. 17, 1990

[86] PCT No.: PCT/JP90/01051

§ 371 Date: May 6, 1991

§ 102(e) Date: May 6, 1991

[87] PCT Pub. No.: WO91/02737

PCT Pub. Date: Mar. 7, 1991

[30] Foreign Application Priority Data

Aug. 18, 1989 [JP] Japan .................. 1-213284

[51] Int. Cl.$^5$ .............. A61K 31/685; A61K 31/66; C07F 9/40; C07F 9/38
[52] U.S. Cl. ................................ 514/76; 514/107; 558/155; 558/161; 562/21
[58] Field of Search ................. 514/76, 107; 558/161; 562/21

[56] References Cited

U.S. PATENT DOCUMENTS 5,043,330 8/1991 Nguyen et al. .................. 514/107

Primary Examiner—Mary C. Lee
Assistant Examiner—Michael G. Ambrose
Attorney, Agent, or Firm—Austin R. Miller

[57] ABSTRACT

This invention relates to a methylenediphosphonic acid compound expressed by the formula (1). The compound has a marked effect as an anti-inflammatory agent or, more particularly, against inflammations accompanying disturbances in bone metabolism.

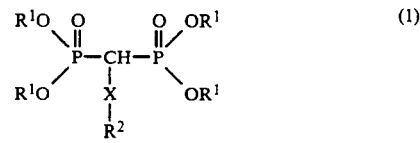

11 Claims, No Drawings

METHYLENEDIPHOSPHONIC ACID COMPOUNDS AND METHODS OF USE FOR THE TREATMENT OF RHEUMATISM AND OSTEOPHOROSIS

TECHNICAL FIELD

This invention relates to a methylenediphosphonic acid compound which is useful as a drug for anti-inflammation and anti-rheumatism.

BACKGROUND ART

Japanese patent application laid-open (kokai) No. SHO 59-42395 discloses a compound similar to the compound of formula (1) according to the present invention, provided X is S and $R^2$ is a non-substituted phenyl group or phenyl group having one or more halogens, nitro group, lower alkyl group, lower alkoxy group, trifluoromethyl, amino group, carboxyl group or alkoxycarbonyl group. However, such compound is not considered to be satisfactory in the effect of anti-inflammation. Also, other compounds of the diphosphonic acid structure are known for anti-inflammation and anti-arthritis by, for example, Japanese Patent Application laid-open (kokai) Nos. SHO 58-174395 and 58-174394. Further, Japanese Patent Application laid-open (kokai) No. SHO 60-174792 reports that 1-substituted amino-1-substituted thioalkyl methylenediphosphonic acid is effective as a anti- rheumatic drug. Still further, clinical demonstrations have been made with disodium (1-hydroxyethylidene)bis-phosphonate as an agent for treatment of osteoporosis. Thus, the compounds of the methylenediphosphonic acid structure have been examined variously as a drug for anti-inflammation or for the treatment of disturbances in calcium metabolism, but further improvement is desired.

On the other hand, inhibitors of cycloxygenase and/or lipoxygenase have been extensively investigated as a new non-steroidal anti-inflammatory drug. In particular, special attention is given to the 2,6-di-tert-butylphenol structure as a dual inhibitor or 5-lipoxygenase inhibitor. For example, there are disclosed 3-(3,5-di-(tert-butyl)-4-hydroxybenzylidene-1-methoxypyrolidine-2-one, etc. in Japanese patent application laid-open Nos. SHO 61-257967, 63-115859 and 63-115960; 3,5-di-tertiary butyl-4-hydroxycinnamamides in Japanese patent application laid-open No. SHO 63-130570; 3,5-di-tert-butyl-4-hydroxystyrene derivatives in Japanese patent application laid-open (kokai) No. SHO 63-24498; 3,5-di-tert-butyl-4-hydroxyphenyl thioether as a substituted phenolic thioether in Japanese patent application laid-open (kokai) No. SHO 63-310821; and 3-(3,5-bis(-tert-butyl)-4-hydroxyphenylthio-propanylpyrrolidine in Japanese patent Application laid-open (kokai) No. SHO 63-310820. But, they are weak in anti-inflammatory effect or have no effect in vivo and are thus scarcely in the level of practical application.

The inventors noted the inhibitors of 5-lipoxygenase in the arachidonate cascade for developing a non-steroidal anti-inflammatory drug and, at the same time, investigated diphosphonic acid as an agent for treatment of disturbances in bone metabolism, and thus found that with an anti-oxidation structure attached to diphosphonic acid, there was produced an effect not found in the conventional drugs for inflammation accompanying disturbances in bone metabolism.

The object of the present invention is to provide a novel compound which is useful as a drug having an excellent anti-inflammatory effect.

Disclosure of the Invention

This invention relates to a methylenediphosphonic acid compound expressed by the formula

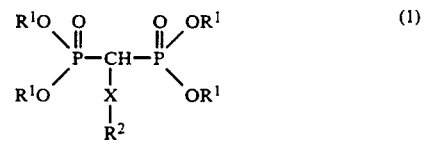 (1)

(in the formula, $R^1$ representing a pharmacologically allowable cation, hydrogen or a straight or branched alkyl group comprising from 1 to 4 carbon atoms, $R^1$'s in the formula being the same or different; X representing $CH_2$ or $S(CH_2)_n$ (n being 0–4); and $R^2$ representing

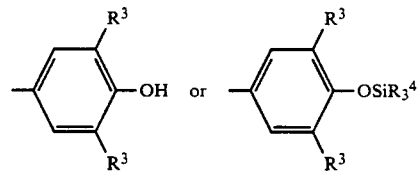

($R^3$ representing a straight or branched alkyl group comprising from 1 to 6 carbon atoms; and $R^4$ representing a straight or branched alkyl group of comprising of 1 to 4 carbon atoms ($R^3$ and $R^4$ may be the same or different))), manufacturing method of said compound and an anti-inflammatory agent containing said compound as an effective component.

Best Mode for Carring Out the Invention

Where $R^1$ is a pharmacologically allowable cation, it may be a metallic cation, ammonium, amine cation or quarternary ammonium cation, and as particularly preferable metallic cations, there may be listed those derived from alkali metals such as, for example, lithium, sodium and potassium, or alkaline-earth metals such as, for example, magnesium and calcium. Cations of other metals such as, for example, aluminum, zinc and iron are of course included according to the present invention. Of these, cations of sodium, potassium and ammonium are more preferable. Also, in $R^1$, the cations may be the same or different, and mixtures of cations and hydrogen such as, for example, mono-cationic salts, di-cationic salts and tri-cationic salts are also included according to the present invention.

For $R^1$, hydrogen, sodium and ammonium are preferable. For the methylenediphosphonic acid compound expressed by formula (1), such compound having all of four $R^1$'s comprised of hydrogen, two comprised of hydrogen and two comprised of cations, or all four comprised of cations is preferable. Particularly preferable is that which has all of $R^1$'s comprised of hydrogen, or has two $R^1$'s comprised of hydrogen and the remaining two $R^1$'s comprised of sodium, or has two $R^1$'s comprised of hydrogen and the remaining two $R^1$'s comprised of ammonium.

According to the present invention, $R^3$ is a straight or branched alkyl group comprising from 1 to 6 carbon atoms, and as such alkyl group, there may be listed methyl group, ethyl group, n-propyl group, isopropyl group, n-butyl group, s-butyl group, t-butyl group and pentyl group.

The compound of the present invention can be produced by the method expressed by the formulas

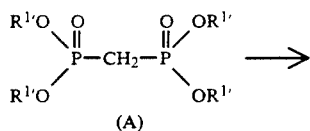
(A)

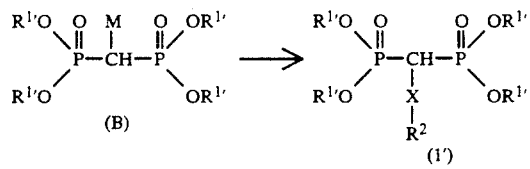
(B)      (1')

[in the formula, $R^{1'}$ representing a lower alkyl; M representing Na, K or Li; and X and $R^2$ being as defined in the foregoing]

The starting material to be used is a lower alkyl ester of methylenediphosphonic acid (A), and the corresponding alkali metal derivative (B) is provided through reaction with an alkali metal introducing agent such as sodium hydride in an adequate solvent such as THF. The reaction is carried out at a temperature of $-70°$ to $50°$ C. In the alkali metal derivative (B) thus obtained, the metal atom M is substituted with a $-X-R^2$ group.

This substitution is carried out through reaction of the alkali metal derivative (B) with a halogen-$CH_2R^2$ in the same solvent used for preparing the alkali metal derivative.

Where X is S, a method of similarly reacting the alkali metal derivative (B) with a disulfide $R^2-S-S-R^2$ is preferably used. The reaction temperature and reaction time may vary greatly with the reagent used. The reaction temperature is from $-70°$ C. to $50°$ C., while the reaction time extends from 2 or 3 hours to several days.

The introduced $R^2$ group has a phenolic hydroxyl group which is a reactive substituent group, and so such substituent group is preferably previously protected with a readily removable reagent such as, for example, a silylating agent, acylating agent or an etherifying agent. Otherwise, an additional amount of an alkali metal introducing agent corresponding to the phenolic hydroxyl group may be added.

From the compound (1') in which $R^{1'}$ is an alkyl group, the compound (1) in which $R^1$ is hydrogen is obtainable by hydrolysis. The hydrolysis is made by reacting the ester with hydrochloric acid for 2 or 3 hours to 24 hours depending on the compound. Or, hydrolysis may be made by treating the ester with trimethylsilyl bromide normally at room temperature.

For economical production of the compound of the present invention in an industrial scale, it is particularly preferable to protect the phenolic hydroxy group by a silylating agent such as trimethylsilylchloride or t-butyldimethylsilylchloride. For example, when an alkali metal derivative (B) of a lower alkyl ester of methylenediphosphonic acid is allowed to react with a disulfide $R^2-S-S-R^2$, di(3,5-di-t-butyl-4-trimethylsiloxyphenyl)disulfide

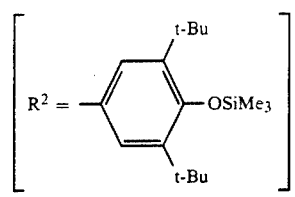

rather than di 3,5-(di-t-butyl-4-hydroxyphenyl)disulfide

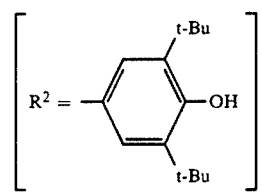

is of less consumption of alkali metal and of less complex reaction to facilitate the purification. Also, in hydrolysis of the ester, if the phenolic hydroxyl group is protected by a trialkylsilyl group such as trimethylsilyl group, the amount of the hydrolytic reagent, trimethylsilyl bromide, is reduced, resulting in economical advantage. From the reason stated above, it is preferable for the manufacturing process of the compound of the present invention to use the phenol protected with a trialkylsilyl group.

After isolation, the acid thus obtained can be converted to a salt thereof by any of the known methods.

The compound of the present invention has a marked anti-inflammatory effect, an anti-pyretic effect; an analgesic effect or an effect to improve bone disorders due to arthritis and osteoporosis and is, therefore, useful as an anti-inflammatory agent, anti-pyretic agent, analgesic agent, anti-rheumatic agent, anti-arthritic agent and anti-osteoporosis agent.

When used for the foregoing purposes, the compound is used directly or as pharmaceutical compositions admixed with a pharmaceutically acceptable carrier or vehicle. Administration may be made orally in the form of a tablet, capsule, powder, granule or pill or non-orally through injection or in the form of a syrup, ointment or suppository. The dose may vary with the object of administration, route of administration and symptoms but is normally about 100 mg to 5 g a day for an adult, preferably about 100 mg to 2 g, and this mount is

EXAMPLES

The following examples are cited for the sake of explaining the present invention and are not restrict the present invention in any way.

EXAMPLE 1

Tetraethyl(3,5-di-t-butyl-4-hydroxyphenylthio)methylene diphosphonate [in the formula (1), $R^1=C_2H_5$, $X=S$ and

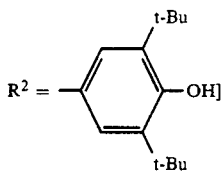

In an atmosphere of argon, 0.752 g of sodium hydride (60% mineral oil dispersion) was washed twice with 5 ml of dry hexane, suspended in 25 ml of dry tetrahydrofuran, and cooled in an ice bath. 2.34 ml of tetraethyl methylene diphosphonate was added. After the evolution of hydrogen ceased, the mixture was stirred at room temperature for 30 minutes. Thereafter, to the mixture cooled in an ice bath, a solution of 5.81 g of 3,5-di-t-butyl-4-trimethylsiloxyphenyldisulfide in 15 ml of tetrahydrofuran was added. The mixture was stirred at room temperature for 3 hours then refluxed for 3 hours. After the addition of 20 ml of 1N hydrochloric acid, the mixture was vigorously stirred for 30 minutes. The organic layer and aqueous layer were separated, and the aqueous layer was extracted three times with 40 ml of ethyl acetate. The combined organic layer was dried over magnesium sulfate, and the solvent was distilled off under reduced pressure. The crude product obtained as residue was purified by silica gel chromatography (silica gel, 160 g; and developing solvent, 4% isopropanol/96% ethyl acetate) to give 3.88 g (76%) of the title compound in an oily form. The compound gradually crystallized into a colorless solid melting at 86°-86.5° C.

NMR (CDCl₃, ppm) δ1.33 (12H, t, J=7.3Hz), 1.40 (18H, s), 3.30 (1H, t, J=22Hz), 4.23 (8H, m), 7.52 (2H, s).

IR (liquid film, cm⁻¹) 3450, 2914, 1576, 1412, 1367, 1245, 1021, 690.

Elemental analysis: As $C_{23}H_{42}O_7SP_2$: Calculated value: C, 52.66; H, 8.07%: Found value: C, 52.48; H, 8.23%.

Example 2

(3,5-di-t-butyl-4-hydroxyphenylthio)methylenediphosphonic acid [in the formula (1), $R^1=H$, $X=S$, and

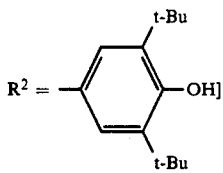

2.78 g of tetraethyl (3,5-di-t-butyl-4-hydroxyphenylthio)methylene diphosphonate obtained in Example 1 was dissolved in 25 ml of dry carbon tetrachloride in an atmosphere of argon, and 5.5 ml of trimethylsilylbromide was added to the solution at room temperature. The mixture was stirred for 72 hours at room temperature, and the solvent was distilled off under reduced pressure. The residue was allowed to stand for 30 minutes under vacuum. 15 ml of methanol was added to the residue and the solvent was distiled off, 1.80 g of the title compound was obtained in the form of a colorless solid (mp 212-213° C. (dec)).

NMR (D₂O, ppm): δ1.38 (18H, s), 3.19 (1H, t, J=20.75Hz), 7.59 (2H, s).

MS (FAB-MS): m/z=413 (M+H).

Elemental analysis: As $C_{15}H_{26}O_7SP_2$ Calculated value: C, 43.69; H, 6.36%. Found value: C, 43.60; H, 6.42%.

Example 3

Tetraethyl 2-(3,5-di-t-butyl-4-hydroxyphenyl)ethylidene-1,1-diphosphonate [in the formula (1), $R^1=C_2H_5$, $X=CH_2$,

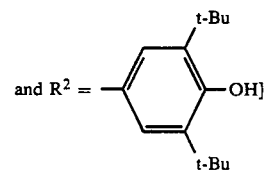

Similarly to Example 1, 1.2 g of sodium hydride (60% mineral oil dispersion) was washed with 5 ml of dry hexane, and dry tetrahydrofuran was added. 3.74 ml of tetraethyl methylene diphosphonate was added to the suspension of NaH in dry THF under ice cooling, the mixture was stirred at room temperature for 30 minutes and then cooled to −78° C. To the mixture, a solution of 3.90 g of 4-chloromethyl-2,6-di-t-butylphenol in 10 ml of tetrahydrofuran was added, and the temperature of the mixture was raised to 0° C. in 3 hours under stirring. 35 ml of 1N hydrochloric acid was added to the mixture, and the organic layer was separated, while the aqueous layer was extracted 3 times with 40 ml of ethyl acetate, and the combined organic layer was dried over magnesium sulfate. The solvent was distilled off under reduced pressure. The crude product obtained was purified by silica gel column chromatography (silica gel, 200 g; and developing solvent, 4% isopropanol/96% ethyl acetate), there was to give 5.93 g (yield, 78%) of the oily title compound.

NMR (CDCl₃, ppm): δ1.26 (12H, t, J=7.3Hz), 1.43 (18H, s), 2.62 (1H, tt, J=23.9Hz, J=4.4Hz), 3.17 (2H, dt, J=4.8Hz, J=17.6Hz), 4.10 (8H, m), 5.08 (1H, s), 7.08 (2H, s).

IR (liquid film, cm¹): 3646, 3318, 2964, 1738, 1479, 1437, 1394, 1367, 1251, 1029, 754.

Elemental analysis: As $C_{24}H_{44}O_7P_2$: Calculated value: C, 56.90; H, 8.76%: Found value: C, 57.14; H, 8.66%.

Example 4

2-(3,5-di-t-butyl-4-hydroxyphenyl)ethylidene-1,1-diphosphonic acid [in the formula (1), $R^1=H$, $X=CH_2$, and

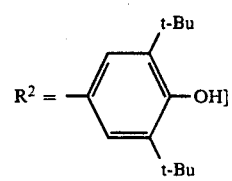

2.88 g of tetraethyl 2-(3,5-di-t-butyl-4-hydroxyphenyl)-ethylidene-1,1-diphosphonate obtained in Example 3 was dissolved in 25 ml of dry carbon tetrachloride, and then 5.9 ml of trimethylsilyl bromide was added at room temperature. The mixture was stirred for 72 hours. After the solvent was distilled off under reduced pressure, the residue obtained was then allowed to stand for 30 minutes under vacuum. 15 ml of methanol was added to the residue, the solvent was distilled off, and a colorless solid was obtained. The solid was washed with an ethyl acetate/hexane (1/5) solvent to afford 1.62 g of the title compound (mp 177°–178° C.).

NMR (acetone-d6, ppm): δ1.40 (18H, s), 2.44 (1H, tt, J=23.93Hz, J=4.39Hz), 3.15 (2H, 1d, J=17.58Hz, J=4.88Hz), 7.17 (2H, s).

IR (KBr, cm$^{-1}$): 3624, 2960, 1437, 1036, 1004, 928.

MS (FAB-MS): m/z=395 (M+H).

Elemental analysis: As $C_{16}H_{28}O_7P_2$: Calculated value: C, 48.73; H, 7.41% Found value: C, 48.79; H, 7.48%.

Example 5

Tetraisopropyl 2-(3,5-di-t-butyl-4-hydroxyphenyl(ethylidene-1,1-diphosphonate [in the formula (1), $R^1$=iPr, X = CH$_2$, and R$^2$ = 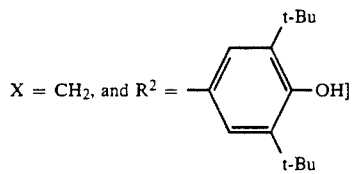 ─OH]

With tetraisopropyl methylenediphosphonate used in place of tetraethyl methylenediphosphonate in Example 3, the procedure was followed. That is, using 1.6 g of sodium hydride (60% mineral oil dispersion), 5.20 g of 4-chloromethyl-2,6-di-t-butylphenol, and 6.61 ml of tetraisopropyl methylenediphosphonate, there was obtained 8.8 g (yield, 78.6%) of the oily title compound.

NMR (CDCl$_3$, ppm): δ1.43 (18H, s), 1.75 (24H, d, J=63.Hz), 2.58 (1H, tt, J=23.9Hz, J=4.4Hz), 3.14 (2H, dt, J=4.8Hz, J=17.6Hz), 4.73 (4H, m), 5.05 (1H, s), 7.06 (2H, s).

Elemental analysis: As $C_{28}H_{52}O_7P_2$: Calculated value: C, 59.77; H, 9.33%: Found value: C, 59.73; H, 9.30%.

Example 6

Tetraethyl(3,5-di-t-butyl-4-trimethylsiloxyphenylthio)-methylene diphosphonate [in the formula (1), $R^1$=C$_2$H$_5$, X = S and R$^2$ = 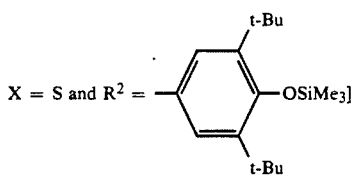 ─OSiMe$_3$]

With 60 ml of dry tetrahydrofuran added, 1.68 g of sodium hydride (60% mineral oil dispersion) was suspended under an atmosphere of argon, and while stirring, 4.74 ml of tetraethyl methylene diphosphonate in 5 ml of dry tetrahydrofuran were added dropwise. After the evolution of hydrogen ceased, 12.38 g of 3,5-di-t-butyl-4-trimethylsiloxylphenyl disulfide dissolved in 15 ml of dry tetrahydrofuran was added. The mixture was refluxed for 5 hours. Cooling to 0° C., the mixture was introduced into ice water and then extracted 3 times with 90 ml of ethyl acetate. The combined organic layer was dried over sodium sulfate, the solvent was distilled off under reduced pressure, and the crude product thus obtained was purified through silica gel column chromatography (silica gel, 45 g; developing solvent, ethyl acetate/isopropanol=100/1-9) to give 7.0 g (yield, 61.7%) of the title compound in the form of a pale yellow oil.

NMR (CDCl$_3$, ppm): δ0.40 (9H, s), 1.39 (12H, t, J=7.0Hz), 1.46 (18H, s), 3.36 (1H, t, J=21.6Hz), 4.29 (8H, m), 7.58 (2H, s).

Elemental analysis: As $C_{26}H_{50}O_7SP_2$: Calculated value: C, 52.33; H, 8.44%. Found value: C, 52.21; H, 8.40%.

Example 7

(3,5-di-t-butyl-4-hydroxyphenylthio)methylenediphosphonic acid [in the formula (1), $R^1$=H, X=S, and R$^2$ = 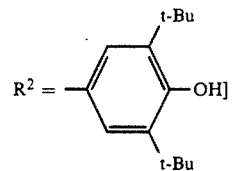 ─OH]

6.0 g of tetraethyl(3,5-di-t-butyl-4-trimethylsiloxyphenylthio)methylene diphosphonate obtained in Example 6 was dissolved in 50 ml of dry carbon tetrachloride under an atmosphere of argon, and 7.8 ml of trimethylsilylbromide was added at room temperature. The mixture was stirred for 72 hours at room temperature, the solvent was distilled off under reduced pressure, and the residue was allowed to stand at room temperature under vacuum for 30 minutes. 30 ml of methanol was added, the solvent was distilled off, and then there was obtained 2.88 g of the title compound in the form of a colorless solid (mp 212°–213° C.).

This compound had the same physical properties with that obtained in Example 2.

Example 8

Disodium(3,5-di-t-butyl-4-hydroxyphenylthio)methylenediphosphonate [in the formula (1), two $R^1$'s being H and the remaining two Na, X=S, and R$^2$ = 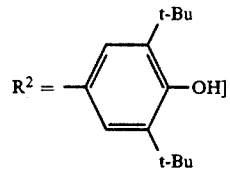 ─OH]

5.009 g of (3,5-di-t-butyl-4-hydroxyphenylthio)-methylenediphosphonic acid was suspended in 250 ml of distilled water, and 47.92 ml of a 0.507N aqueous solution of sodium hydrogencarbonate was slowly added dropwise. Upon completion of the dropwise addition, the mixture was ice cooled and filtered through filter paper. The filtrate was subjected to rotary evaporation. The powder thus obtained was dissolved in 50 ml of water and then frozen in an acetone/dry ice bath. Freeze-drying under vacuum (0.01-0.05 mmHg), there was obtained 4.99 g of the title compound in the form of a white powder.

NMR (D$_2$O, ppm): δ1.40 (18H, s), 3.05 (1H, t, J=19.53Hz), 4.76 (s), 7.60 (2H, s).

Elemental analysis: As C$_{15}$H$_{24}$O$_7$SP Na$_2$.4H$_2$O: Calculated value: C, 34.09; H, 6.11%. Found value: C, 34.08; H, 6.05%

Example 9

Tetraethyl(3,5-dimethyl-4-hydroxyphenylthio)methylenediphosphonate [in formula (1), R$^1$=C$_2$H$_5$, X=S, and

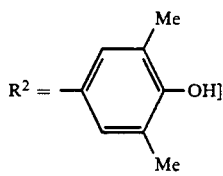

Similarly to Example 1, 0.66 g of sodium hydride (60% mineral oil dispersion) was suspended in 10 ml of dry tetrahydrofuran, and 1.37 ml of tetraethyl methylenediphosphonate was added. A solution of 7.95 g of 3,5-dimethyl-4-trimethylsiloxyphenyl disulfide in 14 ml of dry tetrahydrofuran was added to the mixture.

The reaction mixture was treated similarly to Example 1, and purified by silica gel column chromatography to give 1.11 g (46%) of the title compound as an oily product.

NMR (CDCl$_3$, ppm): δ1.26 (12H, t, J=7.2Hz), 2.19 (6H, s), 3.29 (1H, t, J=23Hz), 4.22 (8H, m), 7.20 (1H, s), 7.23 (2H, s).

Elemental analysis: As C$_{17}$H$_{30}$O$_7$SP$_2$: Calculated value: C, 46.36; H, 6.87%. Found value: C, 46.51; H, 6.93%.

Example 10

(3,5-Dimethyl-4-hydroxyphenylthio)methylene diphosphonate [in the formula (1), R$^1$=H, X=S,

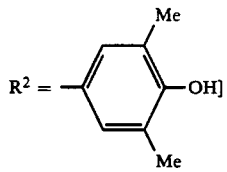

0.726 g of tetraethyl(3,5-dimethyl-4-hydroxyphenylthio)methylene diphosphonate obtained in Example 9 was dissolved in 1.15 ml of dry carbon tetrachloride similarly to Example 2 and reacted with 0.22 ml of trimethylsilylbromide. Treating similarly to Example 2, there was obtained 0.21 g of the title compound in the form of a white solid (mp 238°-239° C.).

NMR (CD$_3$OD, ppm): δ2.18 (6H, s), 3.07 (1H, t, J=23Hz), 4.88 (5H, s), 7.30 (2H, s).

Elemental analysis: As C$_9$H$_{14}$O$_7$SP$_2$: Calculated value: C, 32.93; H, 4.30%. Found value: C, 32.81; H, 4.43%.

Example 11

Tetraethyl(3,5-di-i-propyl-4-hydroxyphenylthio)methylenediphosphonate [in the formula (1), R$^1$=C$_2$H$_5$, X=S, and

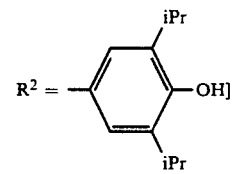

Similarly to Example 1, 2.64 g of sodium hydride (60% mineral oil dispersion) was suspended in 90 ml of dry tetrahydrofuran, and 7.11 ml of tetraethyl methylenediphosphonate in 15 ml of dry tetrahydrofuran was added. Then, a solution of 16.92 g of 3,5-di-i-propyl-4-trimethylsiloxyphenyldisulfide in 15 ml of dry tetrahydrofuran was added to the mixture. Thereafter, the reaction mixture was refluxed for 5 hours, treated according to the conventional method, and purified through silica gel column chromatography to give 5.0 g of the title compound as a pale yellow oily product.

NMR (CDCl$_3$, ppm): δ1.24 (12H, d, J=6.8Hz), 1.34 (12H, t, J=7.3Hz), 1.37 (6H, t, J=6.8Hz), 3.12-3.22 (2H, m), 3.28 (1H, t, J=22Hz), 4.17-4.32 (8H, m), 5.43 (1H, s), 7.35 (2H, s).

IR (liquid film, cm$^{-1}$): 3290, 2968, 2936, 2872, 1464, 1441, 1392, 1367, 1255, 1203, 1160, 1098, 1021, 975.

Elemental analysis: As C$_{21}$H$_{38}$O$_7$SP$_2$: Calculated value: C, 50.80; H, 7.71%. Found value: C, 50.66; H, 7.80%.

Example 12

(3,5-di-i-propyl-4-hydroxyphenylthio)methylenediphosphonic [in the formula (1), R$^1$=H, X=S, and

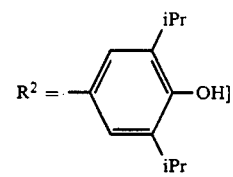

Similarly to Example 7, 2.50 g of tetraethyl (3,5-di-i-propyl-4-hydroxyphenylthio)methylenediphosphonate obtained in Example 11 in 30 ml of carbon tetrachloride was reacted with 6.12 g of trimethylsilylbromide and similarly after-treating, there was obtained 0.87 g of the title compound as a white powder (mp 206°-207° C.).

NMR (CD$_3$OD, ppm): δ1.20 (12H, d, J=6.8Hz), 3.05 (1H, t, J=21Hz), 3.10-3.48 (2H, m), 5.06 (4H, s), 5.47 (1H, s), 7.41 (2H, s).

IR (As$_2$Se$_3$ plate, cm$^{-1}$): 3400, 2968, 2298, 1464, 1441, 1367, 1311, 1201, 1151, 1071, 930.

Elemental analysis: As C$_{13}$H$_{22}$O$_7$SP$_2$: Calculated value: C, 40.63; H, 5.77%. Found value: C, 40.30; H, 5.48%.

Example 13

Tetraethyl 4-(3,5-di-t-butyl-4-hydroxyphenylthio)butylidene-1,1-diphosphonate [in the formula (1), $R^1=C_2H_5$, $X=S(CH_2)_3$, and

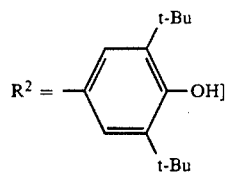

In argon atmosphere, 2.56 g (64.02 mmol) of sodium hydride (60% mineral oil dispersion) was washed with n-pentane (10 ml×2), then suspended in 150 ml of anhydrous toluene and 15.92 ml (64.02 mmol) of tetraethyl methylenediphosphonate was added to the ice cooled suspension. To the reaction mixture was added, at room temperature, 15.30 g (32.01 mmol) of 3-(3,5-di-t-butyl-4-trimethylsiloxyphenylthio)-1-iodopropane dissolved in 40 ml of anhydrous toluene, and the mixture was heated at 85° C. for 4 hours. 150 ml of water was added to the reaction mixture. After adjustment of the mixture to pH 4 with 2N hydrochloric acid, the reaction mixture was extracted with ethyl acetate (200 ml×2, 100 ml×1). The combined organic layer was washed with saturated aqueous sodium chloride solution (200 ml), dried over anhydrous sodium sulfate (25 g), then concentrated. 23.31 g of an oily product was obtained. Purification of the oily product through silica gel column chromatography (Merck, Art. 7734, 240 g, ethyl acetate), gave 4.06 g (7.17 mmol) of tetraethyl 4-(3,5-di-t-butyl-4-hydroxyphenylthio)butylidene-1,1-diphosphonate (yield, 22.4%).

IR (liquid film, cm$^{-1}$): 3302, 2962, 2914, 2874, 1427, 1394, 1367, 1251, 1164, 1027, 971, 866, 789.

NMR (90 MHz, CDCl$_3$, ppm): δ1.32 (12H, t, J=7.03Hz), 1.43 (18H, s), 1.81–2.18 (5H, m), 2.84 (2H, t, J=6.81Hz), 4.00–4.32 (8H, m), 7.22 (2H, s).

MS (m/z, EI): 566 (M$^+$).

Example 14

4-(3,5-di-t-butyl-4-hydroxyphenylthio)-butylidene-1,1-diphosphonic acid-[in the formula (1), $R^1=H$, $X=S(CH_2)_3$, and

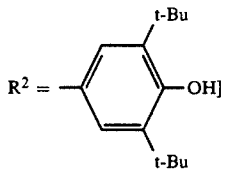

5.622 g (9.93 mmol) of tetraethyl 4-(3,5-di-t-butyl-4-hydroxyphenylthio)-butylidene-1,1-diphosphonate was dissolved in 30 ml of DME, and 5.90 ml (44.69 mmol) of trimethylsilylbromide was added, then the mixture was stirred at room temperature for 3 days in argon atmosphere. 10 ml of methanol was added to the reaction mixture. The mixture was stirred at room temperature for 30 minutes and then concentrated. The residue was dissolved in 40 ml of ether, washed with a saturated aqueous solution of sodium bicarbonate (40 ml×2). The water phase was adjusted to pH 1 with 1N HCl, extracted with ethyl acetate (80 ml×2). The combined organic phase was washed with saturated aqueous solution of sodium chloride (80 ml), dried over anhydrous sodium sulfate (25 g), then concentrated. There was obtained 4.833 g (9.48 mmol) of 4-(3,5-di-t-butyl-4-hydroxyphenylthio)-butylidene-1,1-diphosphonic acid (yield, 95.4%).

IR (KBr, cm$^{-1}$): 3360, 2962, 1427, 1234, 1156, 1122, 1000, 920.

NMR (400 MHz, CD$_3$OD, ppm): δ1.41 (18H, s), 1.84–2.17 (5H, m), 2.77–2.85 (2H, m), 7.22 (2H, s).

MS (m/z, FAB): 453 (M-H).

Comparative Example 2-(4-hydroxyphenyl)ethylidene-1,1-diphosphonic acid [in the formula (1), $R^1=H$, $X=CH_2$, and

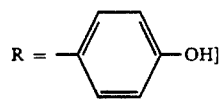

8.8 g of tetraisopropyl 2-(3,5-di-t-butyl-4-hydroxyphenyl)ethylidene-1,1-diphosphonate obtained in Example 5 was suspended in 80 ml of concentrated hydrochloric acid and refluxed for 6 hours. Then, the mixture was cooled to room temperature, hydrogen chloride and water of the mixture were distilled off. The residual solid thus obtained was pulverized and washed with ethyl acetate to give 3.57 g (yield, 81%) of the title colorless compound (mp 196°–198° C.).

NMR (D$_2$O, ppm): δ2.55 (1H, tt, J=22.95Hz, J=6.35Hz), 3.09 (2H, dt, J=6.35Hz, J=16.1Hz), 6.80 (2H, d, J=8.3Hz), 7.19 (2H, d, J=8.3Hz).

Elemental analysis: As C$_8$H$_{12}$O$_7$P$_2$: Calculated value: C, 34.06; H, 4.29%. Found value: C, 34.29; H, 4.25%.

Example 15

Adjuvant arthritis test

When a *Mycobacterium butyricum* adjuvant is injected into a rat, there occurs polyarthritis similar to human rheumatoid arthritis. Using such an adjuvant arthritis model, the anti-inflammatory and anti-rheumatic effects of the compounds of the present invention and the reference were examined according to the following procedure.

0.1 mg of dry dead *Mycobacterium butyricum* was suspended in 0.1 ml of liquid paraffin, and the suspension was injected into the skin of the sole of the left hindpaw of a Lewis female rat, 7-weeks old. The compounds obtained in Examples 2 and 4 and Reference were respectively dissolved in sterilized distilled water and orally administered at a dose of 50 mg per kg of body weight every day for two weeks from the 8th to 21st day after adjuvant injection. The volumes of the left and right hindpaws were measured. Edema density was calculated according to the formula Edema density = [Paw volume of +14 or
+21 day (ml) − Paw volume of +7 day (ml)]/
[paw volume of +7 day (ml)] × 100 and the Edema inhibiting rate was obtained according to the formula

Edema inhibition rate = [Mean edema density of control
group − Mean edema density of compound administered -continued group]/[Mean edema density of control group] × 100 with the results shown in Table 1.

On the 22nd day, the rats were sacrificed, and soft X-ray photos of the left and right hind-legs were taken, and, based on the soft X-ray photos, the extent of bone damage at 5 zones on the left and right hindlegs was evaluated in points of 5 ranks, and the total points were taken as the zonal bone damage index. Further, the zonal bone damage inhibiting rate was calculated according to the formula Zonal bone damage inhibiting rate = [Mean zonal bone
    damage index of control group − Mean zonal bone
    damage index of compound administered group]/
    [Mean zonal bone damage index of control group] × 100 with the results shown in Table 1.

The results thus obtained had ** noted for those which were significant according to the Student t-test and Tukey multiple comparison method with a perilous rate p<0.02 against the control group having only the sterilized distilled water administered and * noted for those which were significant with a perilous rate p<0.05.

As seen from Table 1, the paw edema and bone damage due to primary and secondary inflammation of adjuvant arthritis were inhibited by the compound of the present invention.

TABLE 1

| Compounds | Number of cases | Edema inhibiting rate against control group (%) | | | | Zonal bone damage inhibiting rate against control group (%) +22 day |
|---|---|---|---|---|---|---|
| | | +14 day | | +21 day | | |
| | | Left | Right | Left | Right | |
| Example 2 compound | 6 | 29.2* | 39.7* | 33.8* | 30.4** | 32.5* |
| Example 4 compound | 6 | 2.6 | 31.6 | 9.7 | 21.6 | 29.4* |
| Reference compound | 6 | 4.4 | 7.9 | 0.9 | 6.9 | 0 |

Example 16

Bone resorption inhibition test

With an osteoclast fraction prepared from the hindleg of a mouse placed on a lamella of ivory and stimulated by active-type vitamin $D_3$ there is an resorption lacuna produced on the surface of ivory due to the absorption activity of the osteoclast. Using this absorption model of the bone, the bone resorption inhibiting effect of the compound of the invention was examined according to the following procedure.

5 μl of a suspension of osteoclasts prepared from the hindleg of a mouse was placed on a lamella of ivory and cultured in 500 μl of a 5% calf serum α-added MEM medium containing active-type vitamin $D_3$ ($10^{-10}$M) and the compound of the present invention ($10^6$ or $10^{-5}$M) for 5 days. After culturing, the osteoclasts were removed from the ivory lamella, and the ivory was stained. The total area of resorption lacunae which became obvious by staining was calculated through image analysis. The bone absorption inhibiting rate was calculated by the formula

[Bone resorption inhibiting rate] = [Total area of
    absorption lacunae with active-type vitamin $D_3$ and the
    compound of the invention added ($\mu m^2$)]/Total area of
    resorption lacunae with active-type vitamin $D_3$ added
    ($\mu m^2$)] × 100

As seen from Table 2, the bone resorption of the osteoclasts was inhibited by the compound of the present invention.

TABLE 2

| | Concentration (M) | Bone resorption inhibiting rate against control group |
|---|---|---|
| Example 2 compound | $10^{-6}$ | 48 |
| | $10^{-5}$ | 86 |

Example 17

Acute toxicity test

Using female and male SD rats (5-week age), 6 rats per group, and a 10% aqueous solution of gum arabic for oral administration, and distilled water for intravenous administration as a solvent for the compound to be tested, mortality, during 14 days after administration were recorded, and the $LD_{50}$ values were calculated according to the Miller and Tainter Method (1944). The results are shown in Table 3.

TABLE 3

| | $LD_{50}$ Values (mg/kg) | | | |
|---|---|---|---|---|
| | Example 2 compound | | Example 8 compound | |
| Routes | Male | Female | Male | Female |
| Oral | 652 | 616 | 1871 | 1770 |
| Intravenous | 45.2 | 29.8 | 48.2 | 35.7 |

Industrial Applicability

As described in the foregoing, the methylenediphosphonic acid compound of the present invention has an a marked anti-inflammatory effect, an anti-pyretic and analgesic effect or an effect to improve bone disorders due to rheumatism, arthritis or osteoporosis and is, therefore, useful as an anti-inflammatory agent, anti-pyretic agent, analgesic agent, anti-rheumatic agent, anti-arthritic agent and anti-osteoporosis agent.

We claim:

1. A methylenediphosphonic acid compound expressed by the formula (1)

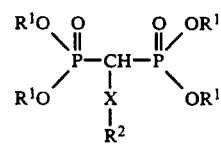

in the formula, $R^1$ representing a pharmacologically allowable cation, hydrogen or a straight or branched alkyl group comprising from 1 to 4 carbon atoms, $R^1$'s being the same or different, X representing $CH_2$ or $S(CH_2)_n$ ($n$ being 0-4) and $R^2$ representing

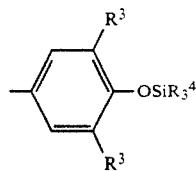

($R^3$ representing a straight or branched alkyl group comprising from 1 to 6 carbon atoms, $R^3$'s being the same or different and $R^4$ representing a straight or branched alkyl group comprising from 1 to 4 carbon atoms, $R^4$'s being the same or different).

2. A methylenediphosphonic acid compound set forth in claim 1 wherein said cation is select ed from the group consisting of lithium, sodium, potassium, magnesium, calcium, aluminum, zinc, iron and ammonium.

3. A methylenediphosphonic acid compound set forth in claim 1 wherein said cation is selected from monocationic salts, dicationic salts and tricationic salts.

4. A method of treating rheumatism comprising administering an effective amount of a methylenediphosphonic acid compound expressed by the formula (1)

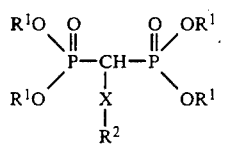

in the formula, $R^1$ representing a pharmacologically allowable cation, hydrogen or a straight or branched alkyl group comprising from 1 to 4 carbon atoms, $R^1$'s being the same or different, X representing $CH_2$ or $S(CH_2)_n$ ($n$ being 0–4) and $R^2$ representing

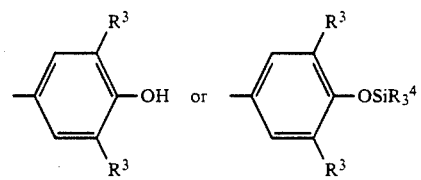

($R^3$ representing a straight or branched alkyl group comprising from 1 to 6 carbon atoms, $R^3$'s being the same or different and $R^4$ representing a straight or branched alkyl group comprising from 1 to 4 carbon atoms, $R^4$'s being the same or different ).

5. A method of treating rheumatism according to claim 4 wherein $R^1$ represents a pharmacologically allowable cation and $R^1$'s may be the same or different, X represents sulfur and $R^2$ represents

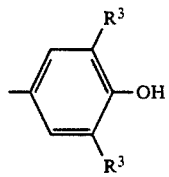

($R^3$ representing a straight or branched alkyl group comprising from 1 to 6 carbon atoms, $R^3$'s being the same or different).

6. A method of treating rheumatism according to claim 4 wherein $R^{1'}$ represents a pharmacologically allowable cation, $R^1$'s being the same or different, X represents sulfur, and $R^2$ represents

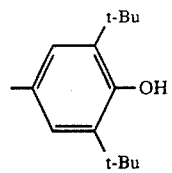

7. A method of treating rheumatism according to claim 4 wherein $R^1$ represents a straight or branched alkyl group comprising from 1 to 4 carbon atoms, $R^1$'s being the same or different, X represents $CH_2$ or $S(CH_2)_n$ ($n$ being 0–4) and $R^2$ represents

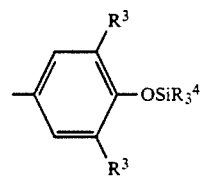

in the formula, $R^3$ representing a straight or branched alkyl group comprising from 1 to 6 carbon atoms, $R^3$'s being the same or different, and $R^4$ representing a straight or branched alkyl group comprising from 1 to 4 carbon atoms, $R^4$'s being the same or different.

8. A method of treating osteoporosis comprising administering an effective amount of a methylenediphosphonic acid compound expressed by the formula (1)

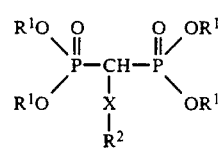

in the formula, $R^1$ representing a pharmacologically allowable cation, hydrogen or a straight or branched alkyl group comprising from 1 to 4 carbon atoms, $R^1$'s being the same or different, X representing $CH_2$ or $S(CH_2)_n$ ($n$ being 0–4) and $R^2$ representing

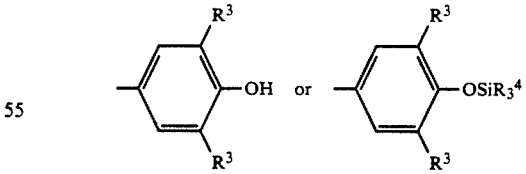

($R^3$ representing a straight or branched alkyl group comprising from 1 to 6 carbon atoms, $R^3$'s being the same or different and $R^4$ representing a straight or branched alkyl group comprising from 1 to 4 carbon atoms, $R^4$'s being the same or different).

9. A method of treating osteoporosis according claim 8 wherein $R^1$ represents a pharmacologically allowable cation and $R^1$'s may be the same or different, X represents sulfur and $R^2$ represents

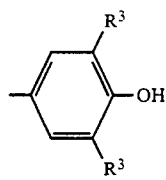

(R³ representing a straight or branched alkyl group comprising from 1 to 6 carbon atoms, R³'s being the same or different).

10. A method of treating osteoporosis according to claim 8 wherein $R^{1'}$ represents a pharmacologically allowable cation, $R^{1'}$'s being the same or different, X represents sulfur, and $R^2$ represents

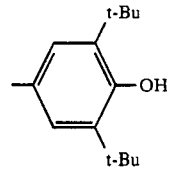

11. A method of treating osteoporosis according to claim 8 wherein $R^1$ represents a straight or branched alkyl group comprising from 1 to 4 carbon atoms, $R^1$'s being the same or different, X represents $CH_2$ or $S(CH_2)_n$ ($n$ being 0–4) and $R^2$ represents

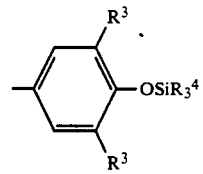

in the formula, $R^3$ representing a straight or branched alkyl group comprising from 1 to 6 carbon atoms, $R^3$'s being the same or different, and $R^4$ representing a straight or branched alkyl group comprising from 1 to 4 carbon atoms, $R^4$'s being the same or different.

* * * * *

UNITED STATES PATENT AND TRADEMARK OFFICE
CERTIFICATE OF CORRECTION

PATENT NO. : 5,153,183
DATED : October 6, 1992
INVENTOR(S) : Norio Kawabe et al

It is certified that error appears in the above-identified patent and that said Letters Patent is hereby corrected as shown below:

In Column 4, at about line 12, please change
"di 3,5-(di-t-butyl-4-hydroxyphenyl)disulfide" to
--di(3,5-di-t-butyl-4-hydroxyphenyl)disulfide--.

In Column 6, line 50, please change "$cm^1$" to --$cm^{-1}$--.

In Column 13, line 64, please change "$10^6$" to --$10^{-6}$--.

On title page, item [54] and col. 1, line 4, change,
"OSTEOPHOROSIS" to --OSTEOPOROSIS--.

Signed and Sealed this

Twenty-fourth Day of August, 1993

Attest:

BRUCE LEHMAN

Attesting Officer

Commissioner of Patents and Trademarks